United States Patent
Lacy

(10) Patent No.: US 6,264,597 B1
(45) Date of Patent: *Jul. 24, 2001

(54) INTRAVASCULAR RADIOTHERAPY EMPLOYING A SAFE LIQUID SUSPENDED SHORT-LIVED SOURCE

(75) Inventor: Jeffrey L. Lacy, Houston, TX (US)

(73) Assignee: Proportional Technologies, Inc., Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/111,960

(22) Filed: Jul. 8, 1998

Related U.S. Application Data

(60) Provisional application No. 60/051,984, filed on Jul. 9, 1997.

(51) Int. Cl.⁷ .................................................. A61N 5/00
(52) U.S. Cl. ................................................................ 600/3
(58) Field of Search ................................................ 600/1–8

(56) References Cited

U.S. PATENT DOCUMENTS

| | | | |
|---|---|---|---|
| 3,324,847 | * 6/1967 | Zoumboulis | 600/3 |
| 5,573,747 | * 11/1996 | Lacy | 424/1.65 |
| 5,616,114 | * 4/1997 | Thornton et al. | 600/3 |
| 5,662,580 | * 9/1997 | Bradshaw et al. | 600/3 |
| 5,674,177 | * 10/1997 | Hehrlein et al. | 600/3 |

* cited by examiner

*Primary Examiner*—Samuel G. Gilbert
(74) *Attorney, Agent, or Firm*—Akin, Gump, Strauss, Hauer & Feld, L.L.P.

(57) ABSTRACT

This invention relates to tissue treatment by intravascular radiation wherein the radiation source is a safe, liquid suspended, short-lived radioisotope. In the procedure of this invention the radioactive material is a suspension of the short-lived isotopes Cu-62 (half-life 9.74 minutes) or Ta-178 (half-live 9.3 minutes).

6 Claims, No Drawings

INTRAVASCULAR RADIOTHERAPY EMPLOYING A SAFE LIQUID SUSPENDED SHORT-LIVED SOURCE

This application claims the benefit of and priority to U.S. Provisional Patent Application Ser. No. 60/051,984, filed Jul. 9, 1997, for which the inventor and title is the same as for the present patent application

BACKGROUND OF THE INVENTION

1. Field of the Invention

This invention relates to tissue treatment by intravascular radiation wherein the radiation source is a safe, liquid suspended, short-lived radioisotope. More specifically this invention is well suited to the radiation treatment of blood vessel walls during or subsequent to their treatment by balloon angioplasty in order to delay or eliminate restenosis thereof.

2. Description of the Related Art

Percutaneous transluminal angioplasty (PTA) treatment of the coronary arteries, percutaneous transluminal coronary angioplasty (PTCA), also known as balloon angioplasty, is the predominant treatment for coronary vessel stenosis.

Popularity of the PTCA procedure is attributable to its relatively high success rate and minimal invasiveness as compared with coronary by-pass surgery. However, patients treated by PTCA suffer from a high incidence of restenosis. About 35% of all patients require repeat PTCA procedures or by-pass surgery, with attendant high cost and added patient risk.

Restenosis occurs as a result of injury to the arterial wall during the lumen-opening angioplasty procedure. The injury initiates a repair response in some patients that is characterized by hyperplastic growth of the vascular smooth muscle cells in the region traumatized by the angioplasty. The hyperplasia of smooth muscle cells narrows the lumen that was opened by the angioplasty, thereby necessitating a repeat PTCA or other procedure to alleviate the restenosis.

Studies have indicated that intravascular radiotherapy (IRT) may be used to prevent stenosis following cardiovascular graft procedures or other trauma to the vessel wall. Proper control of the radiation dosage, however, is critical to impair or arrest hyperplasia without causing excessive damage to healthy tissue.

Radiation dose must be accurately and uniformly applied in order to inhibit smooth muscle cell proliferation while sparing other tissues of the vessel wall. All techniques currently being actually explored with respect to human patients utilize solid long lived sources in the form of thin wires or beads. These sources must be advanced through a thin catheter on the order of 100 cm in length and positioned in the section of artery requiring treatment. Such techniques carry substantial drawbacks in both accuracy and uniformity of dose application as well as in patient safety. Typical arteries being treated are often highly asymmetric. Therefore the wall dose can be circumferentially nonuniform as a result of positioning asymmetry in the absence of precise centering of the source within the artery, which is very difficult to accomplish. Furthermore patient safety is compromised by the risk of lodgement of the source within the vascular system. Although infrequent, such incidents can cost the life of the patient and also can lead to radiation safety risks to health care workers undertaking emergency surgery or other recovery measures.

U.S. Pat. No. 5,616,114 describes a method of intravascular radiotherapy utilizing a liquid suspended radioactive source such as P-32 or I-125. Radiation treatment to a blood vessel wall is accomplished in the preferred embodiment through filling of an intravascular thin-walled balloon with such a source so that intimate contact is achieved between source liquid and the vessel wall.

Filling of a balloon with a radioactive solution in such a way as to achieve intimate contact between the radiation source and the target tissue is a desirable solution to the problem of uniform dose delivery. Although animal studies have clearly demonstrated the feasibility of such technique, no human applications are currently being considered because of the lengthy half lives of commercially available radioactive filling solutions such as P-32 (half life=14 days) and I-125 (half life=60 days). Because of these lengthy half lives and the potential for rupture of the balloon with release of contents into the patient's blood, such isotopes are far too risky to be considered.

In such an event these long-lived sources would distribute and stick in critical tissues such as bone marrow and, because they impart radiation for a lengthy period, can cause death of the patient or substantially increased risks of development of cancers such as leukemia. Accordingly, although elaborate means are described in U.S. Pat. No. 5,616,114 for containment of the source liquid, such procedure as there described has not been utilized on human patients because of this grave danger. Also the level of radioactivity in the solution must be limited to a suboptimal level which requires lengthy treatment times causing further patient risk.

Although an IRT procedure performed through the filling of an intravascular thin-walled balloon with a radioactive source appears to have several advantages with respect to uniformity and location of dosing of that tissue in need of treatment, as heretofore proposed as in U.S. Pat. No. 5,616,114, the extreme dangers involved in balloon rupture within a human patient with its invivo release of the radioactive P-32 and/or I-125 source have precluded its practical use in human patients, even on an experimental basis.

SUMMARY OF THE INVENTION

Described is an improvement upon the art described in U.S. Pat. No. 5,616,114 through use of the short-lived isotopes Cu-62 (half-life=9.74 min) or Ta-178 (half-life=9.3 min) as the source materials for incorporation in the balloon expansion fluid since these isotopes carry essentially no risk of harming the patient through radioactive exposure in the event of balloon rupture and introduction into the blood. The short half-lives of these radioisotopes assure acceptably safe total body and critical organ radiation dose in such an instance. Also described are practical methods for clinical production of the radioactive solution containing the Cu-62 or Ta-178 radioactive isotope in an advantageous chemical form for introduction into the intravascular balloon through use of an automated radio nuclide generator system together with volume concentration means.

DESCRIPTION OF THE PREFERRED EMBODIMENTS

According to the present invention the IRT procedure is accomplished either during or after the angioplasty procedure by advancing a flexible catheter having a balloon at the distal tip through the cardiovascular system of the patient until this treatment balloon is positioned at a target area comprising the stenosed or recently re-opened region of the blood vessel. In the case of simultaneous-angioplasty IRT the treatment balloon is filled with a fluid containing a Cu-62 or Ta-178 radioactive material which simultaneously expands and relieves the stenosis while irradiating the tissue in the target area of the blood vessel. In the case of post-angioplasty IRT the stenosis is first relieved, then the target tissue is irradiated by filling the treatment balloon with the Cu-62 or Ta-178 radioactive fluid until the outer wall of the balloon engages, without substantially expanding, the inner wall of the blood vessel.

In this regard certain of the steps of this invention are like those described in U.S. Pat. No. 5,616,114. However, unlike the procedure as described in that patent wherein the radioactive material is a suspension of beta emitting material, namely I-125 or P-32; in the procedure of this invention the radioactive material is a suspension of the short-lived isotopes Cu-62 (half-life 9.74 minutes) or Ta-178 (half-live 9.3 minutes).

Practical economic delivery of the short lived isotope is achieved through use of a radio nuclide generator system which can repeatedly deliver the required activity level of radioactive solution. This generator is coupled to a concentration and delivery system which conveniently and safely dispenses the required range of concentration of radioactive solution, 50 mCi/ml or higher for Cu-62 and 1000 mCi/ml or higher for Ta-178. The required activity of the isotope is delivered into the angioplasty catheter in a volume slightly greater than or equal to the volume of the inflated balloon (typically 0.14 ml for a 3 mm×20 mm balloon) and flushed into the balloon with a volume of saline flush required to fully inflate the balloon. Efficient and complete delivery into the balloon with little residual in the catheter shaft is thereby accomplished. Radioactivity level of the dispensed solution is measured using a dose calibration system.

Attenuation corrected dose measurement of the actual solution delivered into the balloon is achieved for Cu-62, if desired, by use of a self-calibrating coincidence detector. This technique utilizes the unique characteristics of the positron emitting Cu-62. In such a decay process two 511 keV photons are emitted in opposite directions in every decay. These photons can be detected in coincidence by two small NaI detectors positioned on either side of the patient. Such a detector is only sensitive to emissions originating within a narrow cylinder connecting the two small detectors and not to emissions originating in the catheter shaft or elsewhere. Insertion of a small positron emitting calibration source such as Na-22 near the surface of one of the detectors provides active calibration including effects of attenuation which vary from patient to patient.

Radio nuclide generators are devices which utilize a long lived parent isotope for local production of a short lived isotope in the clinical setting without the need for a local accelerator or reactor production system. The feasibility of such systems are limited by the natural availability of an appropriate parent isotope. Accordingly, only a small number of such systems exist which are compatible with clinical use. The Cu-62 isotope is the sole decay product of Zn-62 whose half life of 9.23 hours is long enough to allow production, preparation of a generator system, and use for at least one day in the clinical setting. A practical implementation of this system for diagnostic applications is described in "Modular Automated Zn-62/Cu-62 PET Radiopharmaceutical Generator" (Lacy, J Nucl Med 36:49P, 1995) in "Cu-62 PTSM and related bis(thiosemicarbazone) complexes produced by an automated Z-62/Cu-62 generator for myocardial PET perfusion imaging" (Lacy, J Nucl Med 37:308P, 1996) and also in commonly owned U.S. Pat. No. 5,573,747 the disclosure of which is hereby incorporated by reference. However, as contemplated for the use intended by this application, the Cu-62 eluted from the generator would be used as such without further binding it to a tissue specific ligand as is the case when the Cu-62 is intended for use in PET imaging. In the application for PET imaging, multiple doses of 15–30 mCi of Cu-62 are produced and administered to patients with acceptable diagnostic level radiation dose. Such doses are limited to less than 5 cGy to the critical organ (the organ receiving the highest dose) and are considered safe for subjects, who often are found to have no significant disease. For a PET imaging application the Cu-62 is produced in a chemical form, Cu-62-PTSM, which causes selective deposition of the isotope in certain tissues including the heart wall (myocardium) and the liver.

For use in intravascular radiation therapy, in accordance with this invention, the Cu-62 will preferably be formulated either in its natural ionic state in water, Cu2+, or as an appropriate chelated form and prepared in a solution compatible with isotonic saline at a concentration required for balloon injection. If such a solution were to enter the patient's blood, as through a rupture of the balloon, the Cu-62, in such forms, effectively binds to proteins in the blood and therefor is not selectively deposited in tissue. Hence, maximum organ dose is reduced even compared with the safe level of that in the diagnostic application of Cu-62-PTSM.

Used in balloon intravascular radiation therapy Cu-62 effectively produces the required uniform local dose to the blood vessel wall as described in U.S. Pat. No. 5,616,114 since Cu-62 decays by positron emission which positron carries a maximum energy of 2.93 meV. This positron produces the same local dose distribution as does a beta particle of equal energy. The higher energy of the Cu-62 positron relative to the 1.71 meV beta of P-32 as employed for the radioactive solution described in U.S. Pat. No. 5,616,114 is advantageous since uniformity of dose is assured deeper into the vessel wall which may be important in cases of strongly asymmetric and thick lesions. For a balloon of fully inflated internal dimensions of 3 mm×20 mm and having a volume of 0.14 ml filled with a Cu-62 containing liquid of total activity 30 mCi (a concentration of 214 mCi/ml) a vessel surface dose in excess of 1500 cGy is achieved in one minute and over 3000 cGy is attained in two minutes. Therefor the range of doses which have been shown to have the desired therapeutic effect can be achieved with safe periods of balloon inflation which causes total occlusion of the artery without the complication of using perfusion catheters which maintain some level of blood flow during inflation but which carry some limiting constraints. Therefore, in accordance with the improvement of this invention, radiation treatment can optionally be carried out simultaneously with inflations for the purpose of clearing the vascular obstruction. Such inflations for coronary artery treatment are typically of one or a few minutes duration.

One important and unique practical factor when deriving isotope from a short lived generator relates to losses due to catheter dead volume. As described in U.S. Pat. No. 5,616,114 (hereafter the "'114 patent") in order to fill the balloon with the radioactive solution, the catheter shaft is evacuated and then the radioactive solution is injected until the balloon is fully inflated. In the procedure of the '114' patent the volume of solution required is equal to the fully inflated balloon volume plus the volume of the lengthy line connecting the balloon with the injection device. In typical balloon catheters, this total volume can be three to five times that of the fully inflated balloon volume. Therefore the total activity which must be delivered by the generator must be 3 to 5 times that of what is required if, instead, the balloon only could be filled with the radioactive source fluid without leaving radioactive solution in the shaft line. This condition can be approached in two ways. The diameter and thus the total volume of this line should be reduced to a minimum. For example, if this line is 0.25 mm inside diameter, which is common in extruded small bore plastic tubing, the volume of a 100 cm shaft line is 0.05 ml. Secondly, special means may be included in the injection system so that the volume of radioactive liquid required to fill the balloon is introduced as a bolus followed by a volume of saline required to displace the shaft dead space. These steps can have a substantial effect on the cost of the generator system, which cost is highly influenced by the amount of Zn-62 loaded on it, which in turn is proportional to the amount of Cu-62 delivered. There is also the beneficial effect of reducing radiation levels in the cath lab and in reduction of dose to the patient from the activity residing in the shaft of the catheter.

The unique characteristics of a Cu-62 positron emitter provides a unique means of absolute measurement of the activity delivered into the balloon thereby compensating for any effects of loss in intervening lines or by dilution with the following saline flush in the above bolus injection technique. In every positron decay a pair of 511 keV gamma rays are emitted at the end of the positron track which is no more than a few mm in length. These gammas can be detected using two small crystal detectors positioned on either side of the patient so that the narrow cylinder connecting the crystals intersects the balloon. Such a detector is sensitive only to activity contained in the balloon and not to that contained in the connecting line largely laying outside of the sensitive geometry. The unique character of the coincidence measurement allows accurate compensation for attenuation of the gamma radiation as it passes out of the patient's body which attenuation is highly dependent on the patient's individual anatomy. This is simply accomplished by placing a calibration positron emitting source near one of the crystals and within the sensitive geometry of the pair. Since one of the two gammas required for the coincidence must pass through the patient along the same path as those emitted from the balloon the count rate obtained per mCi of calibration source is identical to that for a radioactive source located within the patient. This technique facilitates much more accurate quantification of dose than techniques depending on accurate measurement of small volumes in order to determine the actual amount of activity delivered into the balloon. It can be employed in real time to accumulate the dose and to determine the time at which the solution should be evacuated from the balloon. Alternatively, a similar technique can be employed to measure the activity in a holding vessel or line external to the patient just prior to injection into the balloon.

In the generator reported in Lacy, J Nucl Med 36:49P, 1995 and U.S. Pat. No. 5,573,747, the full dose of Cu-62 is contained in about 2 ml of solution which is delivered in 33 seconds. The eluant solution is adjusted to a pH of 5.0 to 7.5, preferably a pH of 5.0–5.5 by in-line addition of an acetate buffering solution by means of a second channel of the pump. In order to achieve the required volume concentration to a volume of 0.14 ml, as in the earlier example, this buffered Cu-62 solution containing Cu-62 2+ is passed through a very small column of less than 0.1 ml volume containing a cation exchange resin, such as Chelex-100, capable of efficiently trapping the Cu-62. The Cu-62 is then washed from this column in a small volume of appropriate eluting solution, such as dilute HCl or an appropriate chelating agent contained in either dilute acid or base, which is then adjusted to physiologic pH and isotonicity. Alternatively a ligand such as EDTA or citrate ion can be combined with the Cu-62 acetate forming an anionic Cu compound which can then be trapped on a small anion column, and washed off with dilute HCl and pH/ion content corrected.

The isotope Ta-178 is the sole decay product of W-178 (half life=22 days). This isotope is an x-ray emitter at dominant energies of 55 keV and 64 keV. Such a source is compatible with effective uniform dose delivery for intravascular radiation therapy. However, because of the much more penetrating nature of the x-ray emissions, relative to the beta or positron radiation, much larger activity levels are required to reach therapeutic doses. The much longer half life of the parent isotope W-178 in this case makes it feasible to supply these much larger activity levels. An activity of 1000 mCi of Ta-178 loaded into the 3 mm×20 mm balloon described previously can provide a therapeutic dose level of 1500 cGy/min with a treatment time of 10 minutes. Such a treatment time can be achieved through use of a perfusion catheter which maintains blood flow during balloon inflation. Concentration of the Ta-178 solution obtained from the generator can be accomplished by addition of NaOH at a level to produce a pH of 12 or greater. This converts the Ta-178 to an anionic form which is readily trapped on a small anion exchange column. The resulting trapped activity in turn is readily washed from this column with 0.1 M HCl which can in turn be pH/ion content adjusted to produce a physiologically compatible Ta-178 solution.

What is claimed is:

1. In an apparatus for localized intravascular radiotherapy of a blood vessel comprising, as a catheter, an elongated member having a proximal and a distal end with the elongated member including an annular fluid passageway and being of a size and of a sufficient flexibility for introduction into a patient's body through a cardiovascular lumen until the distal end is disposed at a target area comprising a wall of the blood vessel; a fluid expansible means connected to the distal end of said elongated member in fluid communication with said fluid passageway; and means for introducing a fluid into said fluid passageway: the improvement comprising, a fluid having as a radioactive material therein Cu-62 or Ta-178.

2. The improved apparatus of claim 1, wherein said fluid has as its radioactive material Cu-62.

3. The improved apparatus of claim 2, wherein said fluid is physiologically isotonic and has a pH in the range of 5.0 to 7.5.

4. The improved apparatus of claim 2, wherein said fluid has a concentration of at least about 214 mCi/ml.

5. The improved apparatus of claim 1, wherein said fluid has as its radioactive material Ta-178 and said catheter is a perfusion catheter which maintains blood flow during expansion of the fluid expansible means.

6. In an apparatus for localized intravascular radiotherapy of a blood vessel comprising, as a catheter, an elongated member having a proximal and a distal end with the elongated member including an annular fluid passageway and being of a size and of a sufficient flexibility for introduction into a patient's body through a cardiovascular lumen until the distal end is disposed at a target area comprising a wall of the blood vessel; a fluid expansible means connected to the distal end of said elongated member in fluid communication with said fluid passageway; and means for introducing a fluid into said fluid passageway: the improvement comprising, a fluid having as a radioactive material therein Cu-62 and a detector sensitive only to gamma rays emitted from said fluid expansible means when filled with said fluid, said detector being positionable relative to said patient during a procedure wherein said fluid expansible means is expanded by said fluid for determining actual radiation dosage delivered to the patient.

* * * * *